US011191779B2

(12) United States Patent
Bae et al.

(10) Patent No.: US 11,191,779 B2
(45) Date of Patent: *Dec. 7, 2021

(54) PHARMACEUTICAL COMPOSITION FOR PREVENTING OR TREATING CANCER, COMPRISING TETRAARSENIC HEXOXIDE CRYSTALLINE POLYMORPH

(71) Applicant: CHEMAS CO., LTD., Seoul (KR)

(72) Inventors: Ill Ju Bae, Gangwon-do (KR); Zenglin Lian, Beijing (CN)

(73) Assignee: CHEMAS CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/467,593

(22) PCT Filed: Dec. 4, 2017

(86) PCT No.: PCT/KR2017/014082
§ 371 (c)(1),
(2) Date: Jun. 7, 2019

(87) PCT Pub. No.: WO2018/105972
PCT Pub. Date: Jun. 14, 2018

(65) Prior Publication Data
US 2020/0000846 A1 Jan. 2, 2020

(30) Foreign Application Priority Data
Dec. 9, 2016 (KR) .......................... 10-2016-0167222

(51) Int. Cl.
*A61K 33/36* (2006.01)
*A61P 35/00* (2006.01)

(52) U.S. Cl.
CPC .............. *A61K 33/36* (2013.01); *A61P 35/00* (2018.01)

(58) Field of Classification Search
CPC ....... A61K 33/36; A61K 31/285; A61P 35/00; C01G 28/005; C01P 2002/72; C01P 2002/60; C01P 2006/80
See application file for complete search history.

(56) References Cited

U.S. PATENT DOCUMENTS

| 2002/0028253 A1 | 3/2002 | Bae et al. |
| 2004/0018246 A1 | 1/2004 | Bae et al. |
| 2004/0213737 A1 | 10/2004 | Huang et al. |
| 2008/0193560 A1 | 8/2008 | Hwang et al. |

FOREIGN PATENT DOCUMENTS

| EP | 0995052 A1 | 11/1999 |
| EP | 1621077 A1 | 2/2006 |
| EP | 3542803 A1 | 9/2019 |
| EP | 3542804 A1 | 9/2019 |
| EP | 3549588 A1 | 10/2019 |
| JP | H11-322616 A | 11/1999 |
| JP | 2020-500219 A | 1/2020 |
| JP | 2020-503372 A | 1/2020 |
| KR | 10-0272835 B1 | 11/2000 |
| KR | 10-2002-0095835 A | 12/2002 |
| KR | 10-2010-0054210 A | 5/2010 |
| WO | 99/24029 A1 | 5/1999 |
| WO | 2002/102814 A1 | 12/2002 |
| WO | 2016/123603 A2 | 8/2016 |
| WO | 2018093215 A1 | 5/2018 |

OTHER PUBLICATIONS

Gilliam, S.J. et al. "Raman spectroscopy of arsenolite: crystalline cubic As4O6" Journal of Solid State Chemistry 173 (2003) 54-58 (Year: 2003).*
Generalic, Eni. "Face-centered cubic lattice." Croatian-English Chemistry Dictionary & Glossary. Oct. 20, 2018. (https://glossary.periodni.com/glossary.php?en=face-centered+cubic+lattice). (Year: 2018).*
Park, M.J. et al. "Tetraarsenic oxide, a novel orally administrable angiogenesis inhibitor" Int. J. Oncol. 22: 1271-1276, 2003 (Year: 2003).*
Raade, G. et al. "Kaatialaite, a new ferric arsenate mineral from Finland" American Mineralogist, vol. 69, pp. 383-387, 1984 (Year: 1984).*
International Search report issued for International Application No. PCT/KR2017/014082 dated Feb. 22, 2018, 6 pages.
Lee, Gwan Hui, "Studies on the Anticancer Activity of Arsenichexoxide(As4O6)" Korea Science and Engineering Foundation Targeted Basic Research Business, Jun. 2003, Grant No. 1350004221, with English language abstract (51 pages).
Office Action issued for corresponding Singapore Patent Application No. 11201904700Q dated Feb. 18, 2020, 5 pages.
Search Report issued in the corresponding European Patent Application No. 17878772.7 dated May 25, 2020, 14 pages.
Office Action issued in the corresponding Canadian Patent Application No. 3044514 dated Jun. 15, 2020, 4 pages.
Anonymous: "Arsenolite R050383—RRUFF Data base: Raman, X-ray, Infrared, and Chemistry", RRUFF database, 2020, Retrieved from the Internet: <URL: https://rruff.info/Arsonolite/R050383> [Retreived on Apr. 23, 2020], 3 pages.
Cameron F. Holder et al., "Tutorial on Powder X-ray Diffraction for Characterizing Nanoscale Materials", ACS Nano, (2019) col. 13, No. 7, pp. 7359-7365.
Zdenka Slejkovec et al., "Arsenic trioxide versus tetraarsenic oxide in biomedical research: misunderstandings and misinterpretations" Biometals, (2012), 25(1), 231-5.
Lee Won Sup et al., "Tetraarsenic hexoxide demonstrates anticancer activity at least in part through suppression of NF-κB activity in SW620 human colon cancer cells", Oncol Rep, (2015), 33 (6): 2940-2946.

(Continued)

*Primary Examiner* — Andrew S Rosenthal
(74) *Attorney, Agent, or Firm* — Rothwell Figg Ernst & Manbeck P.C.

(57) ABSTRACT

The present invention relates to a pharmaceutical composition for preventing or treating cancer and a method for producing same, the composition comprising tetraarsenic hexoxide in which the content of tetraarsenic hexoxide crystalline polymorph a ($As_4O_6$-a) is 99% or more. The composition of the present invention exhibits an excellent cancer cell proliferation inhibition effect and thus can be useful as an anticancer drug.

4 Claims, 6 Drawing Sheets

(56) References Cited

OTHER PUBLICATIONS

Ho-Shin Gwak et al., "Tetraarsenic oxide-induced inhibition of malignant glioma cell invasion in vitro via a decrease in matrix metalloproteinase secretion and protein kinase B phosphorylation" J Neurosurg 2014; 121:1483-1491.

Min Jeong Kim et al, "Arsenic hexoxide enhances TNF-α-induced anticancer effects by inhibiting NF-κB activity at a safe dose in MCF-7 human breast cancer cells" Oncology Reports, 2014; vol. 31, Issue 5, pp. 2305-2311.

* cited by examiner

PHARMACEUTICAL COMPOSITION FOR PREVENTING OR TREATING CANCER, COMPRISING TETRAARSENIC HEXOXIDE CRYSTALLINE POLYMORPH

CROSS-REFERENCE TO RELATED APPLICATIONS

The application is a 35 U.S.C. § 371 National Phase Entry Application from PCT/KR2017/014082, filed on Dec. 4, 2017, which claims the benefit of Korean Patent Application No. 10-2016-0167222 filed on Dec. 9, 2016, the disclosures of which are incorporated herein in their entirety by reference.

TECHNICAL FIELD

The present invention relates to a pharmaceutical composition containing a crystalline polymorph of tetraarsenic hexoxide for prevention or treatment of cancer.

BACKGROUND ART

Cancer is characterized by uncontrolled cell growth, and such abnormal cell growth forms a mass of cells called a tumor, which penetrates into surrounding tissues, and, in severe cases, causes metastasis into other organs of the body. Academically, tumors are called neoplasia. Cancer affects all tissues and organs of the body at various prevalence rates.

The types of cancer may be classified according to tissues and organs in which cancer cells first develop, and may be classified according to shapes and origins of cancer cells. Lung cancer, gastric cancer, colorectal cancer, cervical cancer, and the like are often referred to on the basis of the organs in which the tumor first developed. Also, the types of cancer may be largely divided into connective tissue tumors, epithelial tumors, adenocarcinoma, and the like in an aspect of the origin of cancer cells. In Korea, the most common cancer is thyroid cancer, followed by gastric cancer, colorectal cancer, and lung cancer, in the order of incidence.

Cancer therapies are divided into aggressive therapies of removing cancer tissues solidified in the organs or killing cancer cells and palliative therapies of delaying the development of cancer cells to minimize side effects. In the early stage of cancer development, treatment methods of removing tumors through surgery, chemotherapy, radiotherapy, and the like or killing cancer cells through chemical drugs, radiation, and the like may be selected. However, aggressive therapies have relatively serious side effects in end-stage cancer patients, and thus treatment methods of delaying the development of cancer cells to reduce side effects and improve the quality of life can be selected. In general, anticancer drugs refer to anticancer chemotherapy belonging to aggressive therapies, and include cytotoxic anticancer drugs for killing cancer cells with toxic substances, target cancer drugs of selectively acting on cancer cells and new blood vessels around tissues, and the like (Jung Geun-Young, Introduction and treatment trend of chemotherapy, BRIC View Trend Report, 2016-T20, 2016).

Most anticancer drugs are medicines that show effects by acting on rapidly growing and dividing cancer cells, but cause side effects by attacking even some normal cells showing rapid growth and division. Therapeutic agents that can completely treat cancer have not yet been developed. Therefore, with respect to cancer treatment, there is a continuing need for the development of therapeutic agents having excellent anti-cancer effects.

The present inventors have already received patent rights of technical features wherein tetraarsenic hexoxide purified from natural arsenolite containing arsenic through separation and purification techniques showed cancer metastasis suppressing effects in animal experiments and had excellent anticancer treatment effects when administered to end-stage cancer patients with uterine cancer, bladder cancer, lung cancer, maxillary sinus cancer, kidney cancer, and the like (Korean Patent No. 272835, Novel use of natural chemical substance tetraarsenic hexoxide as novel antitumor drug and pharmaceutical composition thereof, Registered on 30 Aug. 2000).

The present inventors, as a result of continuous research on arsenic, revealed that tetraarsenic hexoxide having 99% or more of tetraarsenic hexoxide crystalline polymorph a can be produced by a novel preparation method, different from the method disclosed in the above registered patent, and a composition containing such tetraarsenic hexoxide has a remarkable effect on cancer prevention or treatment by suppressing the growth of various cancers, and completed the present invention.

DETAILED DESCRIPTION OF THE INVENTION

Technical Problem

An aspect of the present invention is to provide a pharmaceutical composition containing a crystalline polymorph of tetraarsenic hexoxide ($As_4O_6$) as an active ingredient for prevention or treatment of cancer.

Another aspect of the present invention is to provide a method for preparing a pharmaceutical composition containing a crystalline polymorph of tetraarsenic hexoxide ($As_4O_6$) as an active ingredient for prevention or treatment of cancer.

Technical Solution

The present invention is directed to a pharmaceutical composition containing tetraarsenic hexoxide ($As_4O_6$) for prevention or treatment of cancer, wherein the tetraarsenic hexoxide includes 99% or more of tetraarsenic hexoxide crystalline polymorph a ($As_4O_6$-a).

The tetraarsenic hexoxide of the composition may be prepared by: a first step of heating sodium chloride at 100~800° C., followed by cooling; a second step of placing arsenic trioxide ($As_2O_3$) on the sodium chloride, followed by heating from 100° C. to 1000° C. in an airtight state and then cooling; a third step of separating crystals crystallized in a filter bed collecting sublimated arsenic; and a fourth step of repeating the second and third steps four to ten times using the crystals obtained in the third step instead of the arsenic trioxide in the second step, thereby obtaining tetraarsenic hexoxide crystals.

The tetraarsenic hexoxide of composition may contain less than 1% of tetraarsenic hexoxide crystalline polymorph b ($As_4O_6$-b).

The tetraarsenic hexoxide may have a purity of 99.9% or more.

The $As_4O_6$-a and $As_4O_6$-b may have features (i) to (iii) below.

TABLE 1

| Category | Crystalline polymorph a ($As_4O_6$-a) | Crystalline polymorph b ($As_4O_6$-b) |
|---|---|---|
| (i) Cell parameters | a = b = c = 11.0734 Å<br>α = β = γ = 90°<br>V = 1357.82 Å³ | a = b = c = 11.0600 Å<br>α = β = γ = 90°<br>V = 1352.90 Å³ |
| (ii) As—O bond length | 1.786 Å | 2.011 Å |
| (iii) O—As—O bond angle | 98.36° | 109.47° |

Figure 1A:
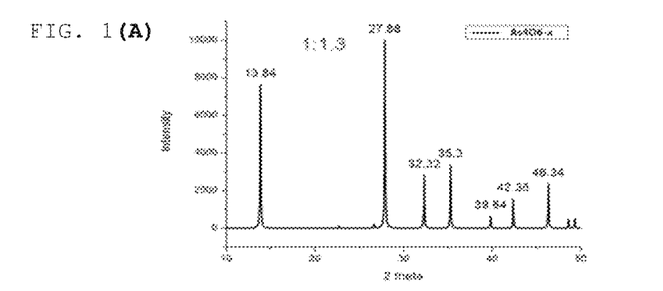
FIGS. 1A-B show X-ray powder diffraction spectra of $As_4O_6$-a and $As_4O_6$-b.
Figure 1B:
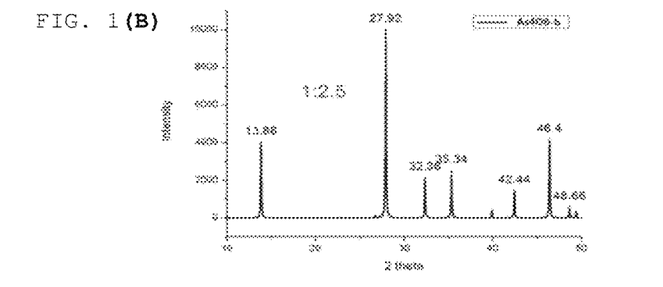

The $As_4O_6$-a has a crystal form, of which the X-ray powder diffraction spectrum obtained by using a light source wavelength of 1.5406 Å within a diffraction angle (2θ) of 10° to 50° at a rate of 1°/min (scan step of 0.02°) shows peaks at 2θ values of 13.84, 27.88, 32.32, 35.3, 39.84, 42.38, 46.34, 48.6, and 49.34 (see FIGS. 1A-B). In addition, the ratio of main peaks shown at 2θ values of 13.8 and 27.9 is 1:1.3.

The $As_4O_6$-b has a crystal form, of which the X-ray powder diffraction spectrum obtained by using a light source wavelength of 1.5406 Å within a diffraction angle (2θ) of 10° to 50° at a rate of 1°/min (scan step of 0.02°) shows peaks at 2θ values of 13.86, 27.92, 32.36, 35.34, 39.9, 42.44, 46.4, 48.66, and 49.4 (see FIGS. 1A-B). In addition, the ratio of main peaks shown at 2θ values of 13.8 and 27.9 is 1:2.5.

The cancer may be selected from the group consisting of lung cancer, esophageal cancer, gastric cancer, colorectal cancer, prostate cancer, pancreatic cancer, cervical cancer, ovarian cancer, and endometrial cancer.

Hereinafter, the present invention will be described in detail.

The present invention is directed to a pharmaceutical composition containing tetraarsenic hexoxide ($As_4O_6$) as an active ingredient for prevention or treatment of cancer, wherein the tetraarsenic hexoxide includes 99% or more of tetraarsenic hexoxide crystalline polymorph a ($As_4O_6$-a).

In accordance with another aspect of the present invention, there is provided a method for preparing a pharmaceutical composition containing a crystalline polymorph of tetraarsenic hexoxide ($As_4O_6$) as an active ingredient for prevention or treatment of cancer, the method including: a first step of heating sodium chloride at 100~800° C., followed by cooling; a second step of placing arsenic trioxide ($As_2O_3$) on the sodium chloride, followed by heating from 100° C. to 1000° C. in an airtight state and then cooling; a third step of separating crystals crystallized in a filter bed collecting sublimated arsenic; and a fourth step of repeating the second and third steps four to ten times using the crystals obtained in the third step instead of the arsenic trioxide in the second step, thereby obtaining tetraarsenic hexoxide crystals, wherein the tetraarsenic hexoxide crystals obtained in the fourth step include 99% or more of tetraarsenic hexoxide crystalline polymorph a ($As_4O_6$-a).

A synthesis reactor of a kaolin material and clamps capable of mounting filters thereon above the synthesis reactor are prepared. Then, sodium chloride is placed in the synthesis reactor, and heated and cooled. The reason why sodium chloride is used in the preparation method of the present invention is that when heating is carried out while arsenic trioxide is placed on the sodium chloride in the second step, heat is uniformly transferred to arsenic compounds, thereby helping the sublimation of the arsenic compounds. In order to remove impurities and moisture from such sodium chloride, the sodium chloride is heated at 100-800° C. for 2-6 hours in the first step. In the first step, the sodium chloride is cooled at room temperature for 3-10 hours after the heating.

Then, the second step is conducted by placing arsenic trioxide ($As_2O_3$) on the sodium chloride, followed by heating from 100° C. to 1000° C. in an airtight state and then cooling. Here, after the placing of arsenic trioxide, three to six filters (filter beds) capable of collecting sublimated arsenic are mounted on the clamps such that the intervals between the filters are 2-6 mm. The filters used herein preferably have a basic weight of 70-100 g/m², a thickness of 0.17-0.25 mm, a filtration speed of 22-30 s/100 ml, and a retention rate of 5-10 μm.

After the mounting of the filters, an airtight state was made, and then a bottom portion of the synthesis reactor is heated for 3-10 hours while the temperature is gradationally raised from 100° C. to 1000° C., so that the temperature of the center portion of the highest filter bed is maintained at 150±100° C., and tetraarsenic hexoxide is crystallized passing through the filter beds. Then, cooling is carried out at room temperature for 5 hours or longer, and preferably 5-10 hours.

Then, the third step is conducted by separating white crystals collected in the three to six spaced filter beds installed in a stacked type.

After a small amount of arsenic trioxide remaining on the sodium chloride in the synthesis reactor is removed, the collected white crystals are placed thereon, and then the second and third steps are repeated four to ten times in the same conditions, thereby finally obtaining tetraarsenic hexoxide crystals. As a result of checking the crystal structures obtained according to the preparation method of the present invention, it was verified that most of the crystals were $As_4O_6$-a, which accounted for 99% or more.

The cancer may be selected from the group consisting of lung cancer, esophageal cancer, gastric cancer, colorectal cancer, prostate cancer, pancreatic cancer, cervical cancer, ovarian cancer, and endometrial cancer.

The pharmaceutical composition containing a crystalline polymorph of tetraarsenic hexoxide of the present invention can be favorably used in the prevention or treatment of cancer.

The pharmaceutical composition of the present invention may be formulated in the form of: an oral formulation, such as a powder, granules, a tablet, a capsule, a suspension, an emulsion, a syrup, or an aerosol; an externally applied preparation; a suppository; and a sterile injectable solution, according to usual methods, respectively. Examples of a carrier, an excipient, and a diluent that may be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may be formulated into preparations by using a diluent or an excipient, such as a filler, an extender, a binder, a wetting agent, a disintegrant, or a surfactant. A solid preparation for oral administration includes a tablet, a pill, a powder, granules, a capsule, and the like. These solid preparations may be prepared by mixing the tetraarsenic hexoxide of the present invention with at least one excipient, for example, starch, calcium carbonate, sucrose or lactose, gelatin, or the like. Also, lubricants, such as magnesium stearate and talc, may be used in addition to simple excipients. A liquid preparation for oral administration corresponds to a suspension, a liquid for internal use, an emulsion, a syrup, and the like, and may include simple diluents that are frequently used, such as water and liquid paraffin, and several excipients, such as a wetting agent, a sweetener, an aromatic agent, and a preservative. A preparation for parenteral administration includes a sterile aqueous solution, a non-aqueous solvent, a suspension, an emulsion, a freeze-drying agent, and a suppository. The non-aqueous solvent and the suspension may include propylene glycol, polyethylene glycol, vegetable oils such as olive oil, injectable esters such as ethylolate, and the like. A base material for the suppository may include Witepsol, Macrogol, Tween 61, cacao butter, laurin butter, glycerogelatin, and the like.

The dose of the pharmaceutical composition may vary depending on age, gender, and body weight of a subject to be treated, a particular disease or pathological condition to be treated, severity of a disease or pathological condition, route of administration, and determination of a prescriber. The determination of the dose based on these factors is within the level of a person skilled in the art, and the general dose is in the range of approximately 0.01-500 mg/kg/day. A more preferable dose is 0.1-100 mg/kg/day. The administration may be carried out once a day or several times in a divided dose a day. The above dose is not intended to restrict the scope of the present invention in any way.

The pharmaceutical composition may be administered to mammals, such as rats, domestic animals, and humans, via various routes. All manners of administration may be predicted, and for example, the administration may be carried out through oral, rectal, intravenous, intramuscular, subcutaneous, endometrial, intracerebroventricular injection.

Advantageous Effects

The pharmaceutical compositions for prevention or treatment of cancer of the present invention have excellent anticancer effects by containing tetraarsenic hexoxide including 99% or more of tetraarsenic hexoxide crystalline polymorph a.

MODE FOR CARRYING OUT THE INVENTION

Hereinafter, preferable examples of the present invention will be described in detail. However, the present invention is not limited to the examples described herein, and thus may be embodied into different forms. Rather, these examples are provided so that this disclosure will be thorough and complete, and will fully convey the scope of the invention to those skilled in the art.

Example 1: Preparation of Present Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10% or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° C. inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm. The filters used herein preferably had a basic weight of 70-100 g/m$^2$, a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour such that the temperature outside the bottom portion of the synthesis reactor was about 350±100° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters.

The collected white crystals were placed on the coarse salt inside the synthesis reactor, and the heating, cooling, and crystal collecting processes were again repeated four times, thereby finally obtaining 12.0 g of the crystals. As a result of checking the structure of the obtained arsenic compound crystals, it was confirmed that most of the crystals were $As_4O_6$-a while 99 wt % or more of $As_4O_6$-a and less than 1 wt % of $As_4O_6$-b were obtained.

It was confirmed that as for the differential scanning calorimetry (DSC) value at a temperature rise rate of 10° C./min, $As_4O_6$-a showed an endothermic peak (melting point) at 282.67° C. and $As_4O_6$-b showed an endothermic peak (melting point) at 286.77° C.

X-ray powder diffraction spectra of $As_4O_6$-a and $As_4O_6$-b are shown in FIGS. 1A-B, and diffraction data of $As_4O_6$-a and $As_4O_6$-b are shown in Table 2 below.

TABLE 2

| $As_4O_6$-a | | $As_4O_6$-b | |
| --- | --- | --- | --- |
| 2θ (°) | Diffraction intensity | 2θ (°) | Diffraction intensity |
| 13.84 | 7631.01 | 13.86 | 4012.09 |
| 27.88 | 10000 | 27.92 | 10000 |
| 32.32 | 2801.74 | 32.36 | 2130.23 |
| 35.3 | 3369.82 | 35.34 | 2511 |
| 39.84 | 623.242 | 39.9 | 447.422 |
| 42.38 | 1551.5 | 42.44 | 1431.86 |
| 46.34 | 2345.2 | 46.4 | 4159.8 |
| 48.6 | 447.69 | 48.66 | 564.995 |
| 49.34 | 502.761 | 49.4 | 375.571 |

As confirmed in FIGS. 1A-B and Table 2, the ratio of main peaks shown at 2θ values of 13.8 and 27.9 was 1:1.3 in $As_4O_6$-a, and the ratio of main peaks shown at 2θ values of 13.8 and 27.9 was 1:2.5 in $As_4O_6$-b. DSC analysis, structure determination, and X-ray diffraction analysis of the prepared compounds were carried out by the following methods.

(1) DSC Analysis

Using a DSC system (SDT Q600 V20.9 Build 20), 20.0 mg of a sample was analyzed while the temperature was raised to 310° C. at a temperature rise rate of 10° C./min with $N_2$ flowing out at 100 mL/min.

(2) X-Ray Crystallography

Single crystals of tetraarsenic hexoxide ($As_4O_6$, MW=395.6) were placed on a glass fiber and then an X-ray beam was applied thereto, to observe diffraction patterns on photographic films and the presence or absence of the organization of diffraction data, thereby determining space groups and cell parameters. Diffraction intensities were collected in the range of 10°<2θ<50°. The crystal structure of $As_4O_6$ was determined from the data by the Patterson method by using a structure determination program (SHELXTL program).

(3) X-Ray Diffractometry

A sample was prepared by pulverizing the obtained crystals into particles having a size of 10-30 μm (−325 mesh), filling a glass holder for X-ray diffraction analysis (20 mm×16 mm×1 mm) with the particles, compressing the particles by a glass slide or the like, and flattening the particles to allow a sample surface to be parallel with a holder surface. The X-ray diffraction spectrum of the crystals was drawn using Cu Kα$_1$ (1.54060 Å) of XRD within a diffraction angle (2θ) of 10° to 50° at a rate of 1°/min (scan step of 0.02°).

Comparative Example 1: Preparation of Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10% or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° C. inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm The filters used herein preferably had a basic weight of 70-100 g/m$^2$, a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour such that the temperature outside the bottom portion of the synthesis reactor was about 350±100° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters. 48.5 g of crystals were collected from the filters. As a result of checking the crystal structure of the collected arsenic compounds, it was confirmed that $As_4O_6$-b accounted for 99 wt % or more.

Comparative Examples 2 to 4: Preparation of Tetraarsenic Hexoxide

Comparative Examples 2 and 3 were prepared by mixing Example 1 (composition having 99% or more of crystalline polymorph $As_4O_6$-a) and Comparative Example 1 (composition having 99% or more of crystalline polymorph $As_4O_6$-b) at 4:1 and 1:1, respectively.

Test Example 1: Test on Human Cancer Cell Proliferation Inhibitory Effects (1) Materials and Cell Culture Fetal bovine serum (FBS) and cell culture medium were prepared (Hyclone), and dimethyl sulfoxide (DMSO) and 3-(4,5-dimethyl-thiazol-2yl)-2,5-diphenyltetrazolium bromide (MTT, Amresco LLC, USC) were prepared.

As human cancer cell lines, human lung cancer cell lines NCL-H226 and SK-MES-1, human esophageal cancer cell lines KYSE-150 and TE-1, human gastric cancer cell line AGS, human colorectal cancer cell lines HT29 and HCT116, human prostate cancer cell line PC-3, human pancreatic cancer cell lines BxPC-3 and PANC-1, human cervical cancer cell lines SiHa and HeLa, human ovarian cancer cell line SK-OV-3, and human endometrial cancer cell lines Ishikawa, HEC-1A, and HEC-1B were obtained from the Shanghai Cell Bank of Chinese Academy of Sciences. The cells were incubated in media supplemented with 10% FBS, 50 U/ml penicillin, and 50 µg/ml streptomycin and suitable for incubation of respective cells (RPMI-1640 (NCL-H226, TE-1, BxPC-3, Ishikawa), MEM (SK-MES-1, SiHa, HeLa, HEC-1B), Ham's F-12K (AGS), Ham's F-12 (PC-3), McCOY's 5A (HT29, HCT116, SK-OV-3, HEC-1A), RPMI-1640:Ham's F-12=1:1(v:v) (KYSE-150), and DMEM (PANC-1)) in a humidified incubator with 5% $CO_2$ and 95% air. The media were exchanged every three days.

(2) Cell Proliferation Assay (MTT Assay)

The effects of Example 1 and Comparative Examples 1 to 3 on cell proliferation were assessed using MTT assay. MTT assay is based on the ability of viable cells against MTT to produce insoluble dark blue formazan products. After the cells were suspended in the medium by trypsin treatment and collected, the cells were dispensed at a density of $4 \times 10^3$ cells/well in a 96-well culture dish (Costar, Cambridge, Mass., USA). After 24 hours, the cells in the media containing 10% FBS were treated with Example 1 and Comparative Examples 1 to 3, at 0, 0.625, 1.25, 2.5, 5, 10, 20, 40, or 80 µM, and then incubated. Here, stock solutions obtained by dissolving Example 1 and Comparative Examples 1 to 3 at $5 \times 10^{-2}$ M in 1 M sodium hydroxide was used. For MTT assay for cell proliferation, supernatants were removed from the cells incubated for 24 hours, 48 hours, and 72 hours after the sample treatment, and 20 µl of 5 mg/ml MTT solution was added per well, and the cells were incubated at 37° C. for 4 hours to form formazan crystals. After the incubation, supernatants were again removed, followed by addition of 100 µl of DMSO to every well, and then mixing was carried out to completely dissolve dark blue crystals. All the crystals were completely dissolved by standing at room temperature for 15 minutes, and the absorbance was measured using a micro-plate reader at a wavelength of 570 nm ($A_{570\ nm}$).

(3) Statistical Analysis

The absorbance value of the control group treated without the sample was calculated as 100, and the absorbance value of the treatment group treated with the sample, compared with that of the control group, was calibrated, and the percentage of inhibition of cell proliferation was calculated according to the following equation.

Percentage (%) of inhibition of cell proliferation=
((mean absorbance of control group cells−mean absorbance of treatment group cells)/mean absorbance of control group cells)×100

All data were expressed as mean±standard error of the mean (mean±SEM). One-way analysis of variance (ANOVA) followed by Dunnett's post-test was used to perform multiple comparison. Statistical significance was defined as $p<0.05$, and each test was repeated three times.

(4) Results of Investigating Inhibition of Lung Cancer Cell Line Proliferation

Figure 2:
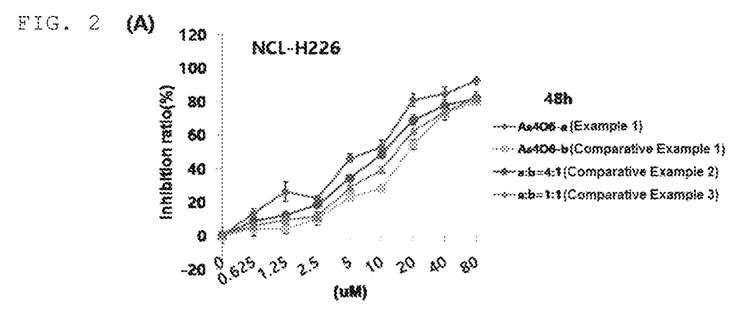
FIGS. 2A-B show graphs depicting the results of assessing cell proliferation inhibitory effects after the lung cancer cell line NCL-H226 was treated with Example 1 and Comparative Examples 1 to 3 and incubated for 48 hours (FIG. 2A) and 72 hours (FIG. 2B).
Figure 3:
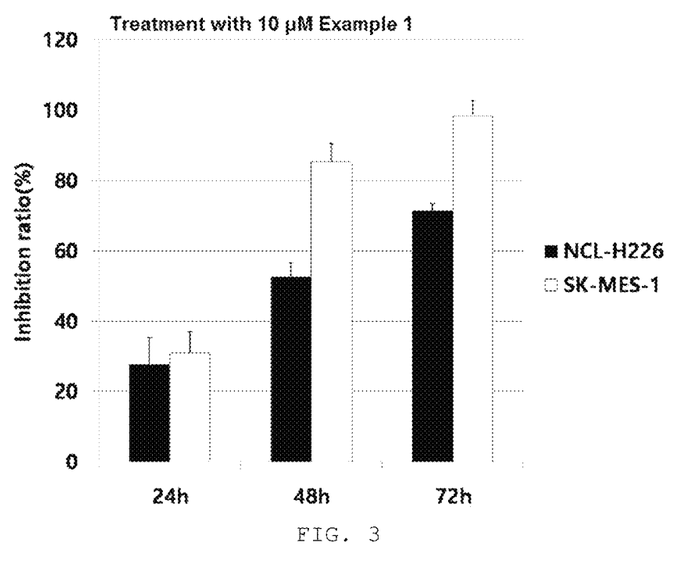
FIG. 3 shows a graph depicting the results of assessing lung cancer cell proliferation inhibitory effects according to treatment time when the lung cancer cell lines NCL-H226 and SK-MES-1 were treated with 10 μM Example 1.

The human lung cancer cell lines NCL-H226 and SK-MES-1 were treated with Example 1 and Comparative Examples 1 to 3, and incubated for 24, 48, and 72 hours, followed by MTT assay. The results obtained using NCL-H226 are shown in FIGS. 2A-B and 3.

All of the test results obtained by treating NCL-H226 with Example 1 and Comparative Examples 1 to 3 and then incubating the cells for 48 hours (FIG. 2A) and 72 hours (FIG. 2B) confirmed that the percentages of inhibition of the lung cancer cell line NCL-H226 proliferation were higher in the treatment with Example 1 than the treatment with Comparative Examples 1 to 3.

In addition, as a result of investigating the inhibition of cancer cell proliferation according to treatment time when the lung cancer cell lines NCL-H226 and SK-MES-1 were treated with 10 µM Example 1 (FIG. 3), it was confirmed that the percentage of inhibition of cell proliferation was increased with the treatment time in both of NCL-H226 and SK-MES-1.

(5) Results of Investigating Inhibition of Esophageal Cancer Line Proliferation

Figure 4:
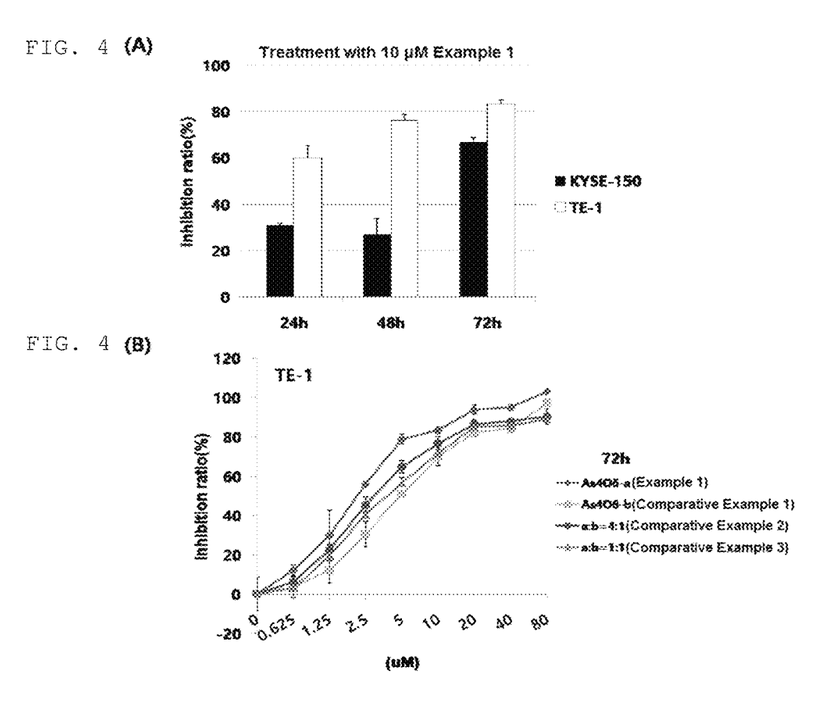
FIGS. 4A-B show graphs depicting the results of assessing esophageal cancer cell proliferation inhibitory effects according to treatment time when the esophageal cancer cell lines KYSE-150 and TE-1 were treated with 10 μM Example 1 (FIG. 4A) and cell proliferation inhibitory effects after TE-1 was treated with Example 1 and Comparative Examples 1 to 3 and then incubated for 72 hours (FIG. 4B).

The human esophageal cancer cell lines KYSE-150 and TE-1 were treated with Example 1 and Comparative Examples 1 to 3, and incubated for 24, 48, and 72 hours, followed by MTT assay. The results are shown in FIGS. 4A-B.

As a result of investigating the inhibition of cancer cell proliferation according to treatment time after KYSE-150 and TE-1 were treated with 10 µM Example 1 (FIG. 4A), it was confirmed that in the case of the esophageal cancer cell line TE-1, the percentage of inhibition of cell proliferation was increased with the treatment time, and in the case of the esophageal cancer cell line KYSE-150, there is no great difference in percentage of inhibition of cell proliferation between the treatment for 24 hours and the treatment for 48 hours, but the percentage of inhibition of cell proliferation was significantly increased in the treatment for 72 hours.

In addition, all of the test results obtained by treating TE-1 with Example 1 and Comparative Examples 1 to 3 and then incubating the cells for 72 hours (FIG. 4B) confirmed that the percentage of inhibition of the esophageal cancer cell line TE-1 proliferation was higher in the treatment with Example 1 than the treatment with Comparative Examples 1 to 3.

(6) Results of Investigating Inhibition of Gastric Cancer Line Proliferation

Figure 5:
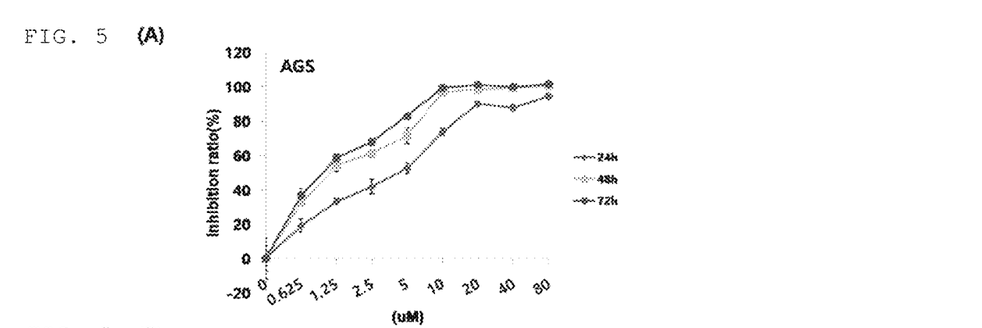
FIGS. 5A-B show graphs depicting the results of assessing gastric cancer cell proliferation inhibitory effects according to concentration of Example 1 and treatment time when the gastric cancer cell line AGS was treated with Example 1 (FIG. 5A) and cell proliferation inhibitory effects after AGS was treated with Example 1 and Comparative Examples 1 to 3 and then incubated for 72 hours (FIG. 5B).

The human gastric cancer cell line AGS was treated with Example 1 and Comparative Examples 1 to 3, and incubated for 24, 48, and 72 hours, followed by MTT assay. The results are shown in FIGS. 5A-B.

As a result of investigating the inhibition of cancer cell proliferation according to treatment time when the gastric cancer cell line AGS was treated with Example 1 of different concentrations (FIG. 5A), it was confirmed that the inhibition of cell proliferation was increased with the treatment time at each treatment concentration, and the percentage of inhibition of gastric cancer cell proliferation was high in spite of the treatment for only 48 hours.

In addition, all of the test results obtained by treating AGS with Example 1 and Comparative Examples 1 to 3 and then incubating the cells for 72 hours (FIG. 5B) confirmed that the percentage of inhibition of gastric cancer cell line AGS proliferation was higher in the treatment with Example 1 than the treatment with Comparative Examples 1 to 3.

Figure 6:
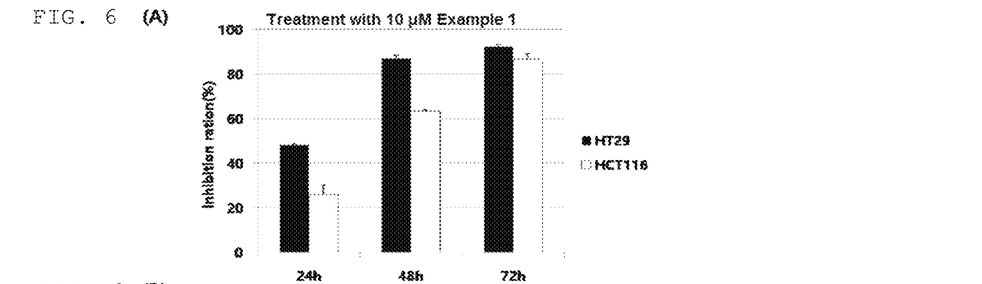
FIGS. 6A-B show graphs depicting the results of assessing colorectal cancer cell proliferation inhibitory effects according to treatment time when the colorectal cancer cell lines HT29 and HCT116 were treated with 10 μM Example 1 (FIG. 6A) and cell proliferation inhibitory effects after HT29 was treated with Example 1 and Comparative Examples 1 to 3 and then incubated for 72 hours (FIG. 6B).

(7) Results of Investigating Inhibition of Colorectal Cancer Cell Line Proliferation The human colorectal cancer cell lines HT29 and HCT116 were treated with Example 1 and Comparative Examples 1 to 3, and incubated for 24, 48, and 72 hours, followed by MTT assay. The results are shown in FIGS. 6A-B.

As a result of investigating the inhibition of cancer cell proliferation according to treatment time when HT29 and HCT116 were treated with 10 μM Example 1 (FIG. 6A), it was confirmed that the percentage of inhibition of cell proliferation was increased with the treatment time in both HT29 and HCT116.

In addition, all of the test results obtained by treating HT29 with Example 1 and Comparative Examples 1 to 3 and then incubating the cells for 72 hours (FIG. 6B) confirmed that the percentage of inhibition of the colorectal cancer cell line HT29 proliferation was higher in the treatment with Example 1 than the treatment with Comparative Examples 1 to 3.

Figure 7:
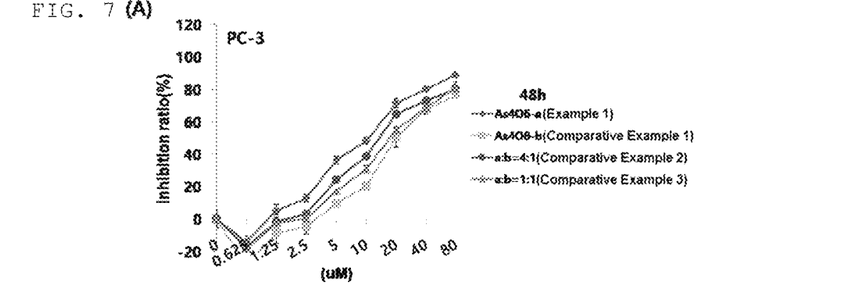
FIGS. 7A-B show graphs depicting the results of assessing cell proliferation inhibitory effects after the prostate cancer cell line PC-3 was treated with Example 1 and Comparative Examples 1 to 3 and incubated for 48 hours (FIG. 7A) and 72 hours (FIG. 7B).

(8) Results of Investigating Inhibition of Prostate Cancer Cell Line Proliferation The prostate cancer cell line PC-3 was treated with Example 1 and Comparative Examples 1 to 3, and incubated for 48 and 72 hours, followed by MTT assay. The results are shown in FIGS. 7A-B.

All of the test results obtained by treating PC-3 with Example 1 and Comparative Examples 1 to 3 and then incubating the cells for 48 hours (FIG. 7A) and 72 hours (FIG. 7B) confirmed that the percentage of inhibition of the prostate cancer cell line PC-3 proliferation was higher in the treatment with Example 1 than the treatment with Comparative Examples 1 to 3.

Figure 8:
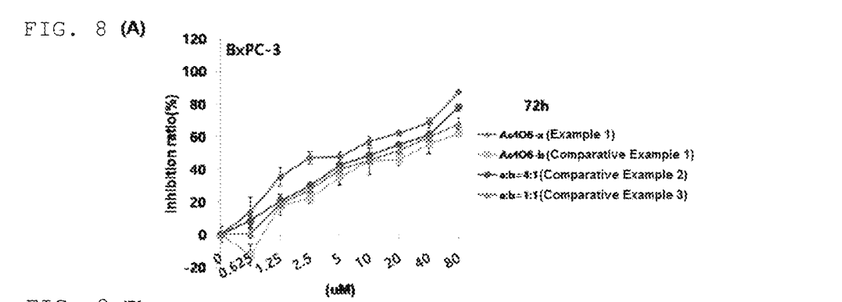
FIGS. 8A-B show graphs depicting the results of assessing cell proliferation inhibitory effects after the pancreatic cancer cell line BxPC-3 was treated with Example 1 and Comparative Examples 1 to 3 and incubated for 72 hours (FIG. 8A) and cell proliferation inhibitory effects after the pancreatic cancer cell lines BxPC-3 and PANC-1 were treated with Example 1 of different concentrations and incubated for 72 hours (FIG. 8B).

(9) Results of Investigating Inhibition of Pancreatic Cancer Cell Line Proliferation The human pancreatic cancer cell lines BxPC-3 and PANC-1 were treated with Example 1 and Comparative Examples 1 to 3, and incubated for 24, 48, and 72 hours, followed by MTT assay. The results are shown in FIGS. 8A-B.

All of the test results obtained by treating BxPC-3 with Example 1 and Comparative Examples 1 to 3 and then incubating the cells for 72 hours (FIG. 8A) confirmed that the percentage of inhibition of the pancreatic cancer cell line BxPC-3 proliferation was higher in the treatment with Example 1 than the treatment with Comparative Examples 1 to 3.

In addition, the test results obtained by treating the pancreatic cancer cell lines BxPC-3 and PANC-1 with Example 1 according to concentration of Example 1 and then incubating the cells for 72 hours (FIG. 8B) confirmed that the percentage of inhibition of cell proliferation was increased dependent on the concentration of Example 1 in both BxPC-3 and PANC-1.

Figure 9:
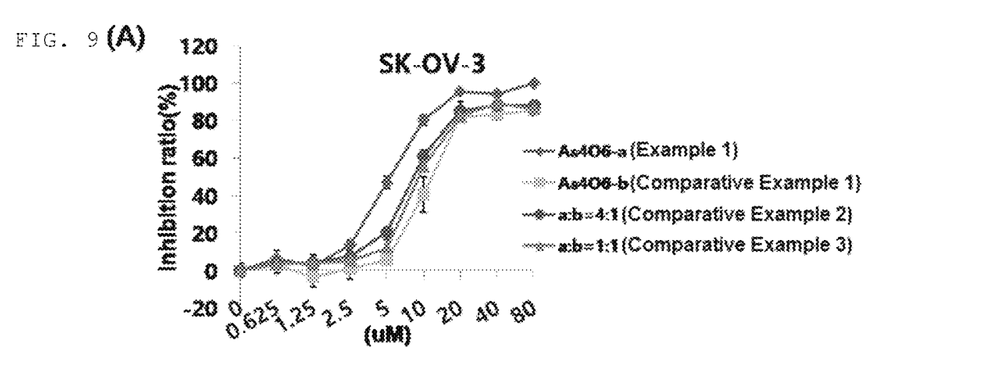
FIGS. 9A-C show graphs depicting the results of assessing the cell proliferation inhibition after the ovarian cancer cell line SK-OV-3 (FIG. 9A), the human cervical cancer cell line HeLa (FIG. 9B), and the human endometrial cancer cell line HEC-1B (FIG. 9C) were treated with Example 1 and Comparative Examples 1 to 3 and then incubated for 72 hours.

(10) Results of Investigating Inhibition of Ovarian, Cervical, and Endometrial Cancer Cell Proliferation The human ovarian cancer cell line SK-OV-3, the human cervical cancer cell lines SiHa and HeLa, and the human endometrial cancer cell lines Ishikawa, HEC-1A, and HEC-1B were treated with Example 1 and Comparative Examples 1 to 3, and incubated for 72 hours, followed by MTT assay. The results are shown in FIGS. 9A-C.

All of the test results obtained by treating the human ovarian cancer cell line SK-OV-3 (FIG. 9A), the human cervical cancer cell line HeLa (FIG. 9B), and the human endometrial cancer cell line HEC-1B (FIG. 9C) with Example 1 and Comparative Examples 1 to 3 and then incubating the cells for 72 hours confirmed that the percentages of inhibition of the ovarian, cervical, and endometrial cancer cell proliferation were higher in the treatment with Example 1 than the treatment with Comparative Examples 1 to 3.

(11) Comparison of Cell Proliferation Inhibitory Activity in Various Cancer Cell Lines $IC_{50}$ values of Example 1 were analyzed on the basis of the test results obtained by the treatment with Example 1 for 72 hours in the test results obtained through the tests of inhibition of the human lung, esophageal, gastric, colorectal, prostate, pancreatic, ovarian, cervical, and endometrial cancer cells proliferation. The analysis results are shown in Table 3 and FIG. 10.

TABLE 3

| Cancer type | Cell line | Cancer cell growth inhibition ($IC_{50}$, μM) |
| --- | --- | --- |
| Lung cancer | NCL-H226 | 5.12 |
|  | SK-MES-1 | 2.47 |
| Esophageal cancer | KYSE-150 | 9.85 |
|  | TE-1 | 2.35 |
| Gastric cancer | AGS | 0.9 |
| Colorectal cancer | HT29 | 1.27 |
|  | HCT116 | 5.07 |
| Prostate cancer | PC-3 | 4.98 |
| Pancreatic cancer | BxPC-3 | 4.98 |
|  | PANC-1 | 5.62 |
| Cervical cancer | SiHa | 2.8 |
|  | HeLa | 1.63 |
| Ovarian cancer | SK-OV-3 | 5.02 |
| Endometrial cancer | Ishikawa | 2.75 |
|  | HEC-1A | 2.47 |
|  | HEC-1B | 4.61 |

Figure 10:
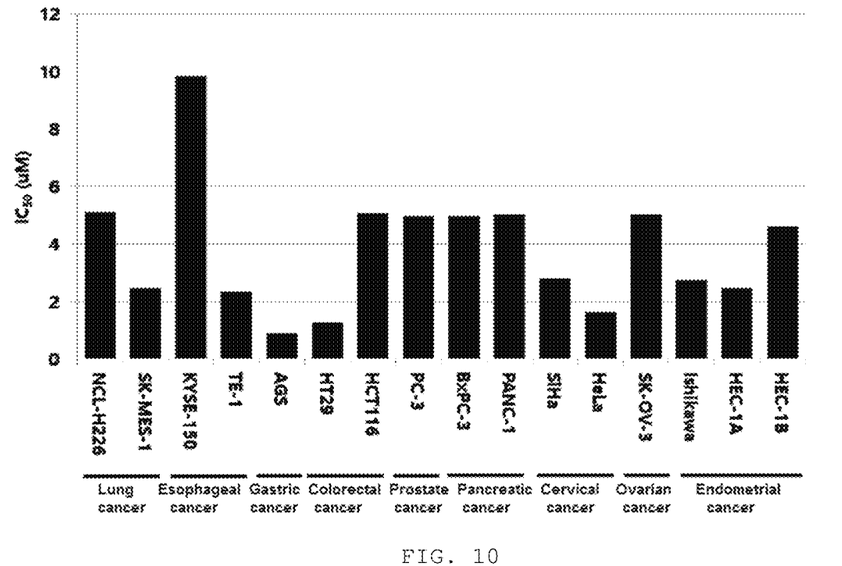
FIG. 10 shows a graph depicting the results of comparing, through $IC_{50}$ values, cell proliferation inhibition degrees of Example 1 in human lung, esophageal, gastric, colorectal, prostate, pancreatic, cervical, ovarian, and endometrial cancer cell lines.

As can be seen from Table 3 and FIG. 10, the $IC_{50}$ values of Example 1, which are associated with cancer cell proliferation inhibitory activity, had low concentrations in all of the types of cancer.

Although not shown in the present invention, the tetraarsenic hexoxide of the present invention was confirmed to inhibit the proliferation of various cancer cells, such as brain cancer, breast cancer, liver cancer, and skin cancer.

Therefore, it can be seen that Example 1 showed excellent anticancer effects by inhibiting the growth of cancer cells in various cancers, such as lung cancer, esophageal cancer, gastric cancer, colorectal cancer, prostate cancer, pancreatic cancer, cervical cancer, ovarian cancer, and endometrial cancer.

The invention claimed is:

1. A pharmaceutical composition containing tetraarsenic hexoxide (As4O6) as an active ingredient for treatment of cancer, wherein the tetraarsenic hexoxide includes 99 wt % or more of tetraarsenic hexoxide crystalline polymorph a having features (i) to (iii) below:
   (i) Cell parameters:
   $a=b=c=11.0734$ Å
   $\alpha=\beta=\gamma=90°$
   $V=1357.82$ Å$^3$
   (ii) As-O bond length: 1.786 Å
   (iii) O-As-O bond angle: 98.36°,
   wherein the pharmaceutical composition further comprises at least one of a carrier, a diluent, and an excipient,
   wherein in an X-ray powder diffraction spectrum of the crystalline polymorph a, obtained by using a light source wavelength of 1.5406 Å within a diffraction angle (2θ) of 10° to 50° at a rate of 1°/min (can step of 0.02°), peaks are shown at 2θ values of 13.84, 27.88, 32.32, 35.3, 39.84, 42.38, 46.34, 48.6, and 49.34,
   wherein the tetraarsenic hexoxide is prepared by:
   a first step of heating sodium chloride at 100~800° C., followed by cooling;
   a second step of placing arsenic trioxide (As$_2$O$_3$) on the sodium chloride, followed by heating from 100° C. to 1000° C. in an airtight state and then cooling;
   a third step of separating crystals crystallized in a filter bed collecting sublimated arsenic; and
   a fourth step of repeating the second and third steps four to ten times using the crystals obtained in the third step instead of the arsenic trioxide in the second step, thereby obtaining the tetraarsenic hexoxide including 99 wt % or more of tetraarsenic hexoxide crystalline polymorph a, and
   wherein the carrier, the diluent, and the excipient do not include water.

2. The pharmaceutical composition of claim 1, wherein the tetraarsenic hexoxide has a purity of 99.9% or higher.

3. The pharmaceutical composition of claim 1, wherein the cancer is selected from the group consisting of lung cancer, esophageal cancer, gastric cancer, colorectal cancer, prostate cancer, pancreatic cancer, cervical cancer, ovarian cancer, and endometrial cancer.

4. The pharmaceutical composition of claim 1, wherein the carrier, the diluent, or the excipient is at least one of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, methyl hydroxybenzoate, propyl hydroxybenzoate, talc, magnesium stearate, mineral oil, propylene glycol, polyethylene glycol, vegetable oils, injectable esters, wax, polyethylene glycol, polysorbate 61, cacao butter, laurin butter, and glycerogelatin.

* * * * *